(12) United States Patent
Woods (10) Patent No.: US 10,790,059 B2
(45) Date of Patent: *Sep. 29, 2020

(54) METHOD AND APPARATUS FOR SHARING MEDICAL INFORMATION

(71) Applicant: 3 NET WISE, INC., Fort Wayne, IN (US)

(72) Inventor: Sherrod A. Woods, Fort Wayne, IN (US)

(73) Assignee: 3 NET WISE, INC., Fort Wayne, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/785,375

(22) Filed: Feb. 7, 2020

(65) Prior Publication Data

US 2020/0176111 A1 Jun. 4, 2020

Related U.S. Application Data

(63) Continuation of application No. 15/996,474, filed on Jun. 2, 2018, which is a continuation of application
(Continued)

(51) Int. Cl.
| | |
|---|---|
| *G16H 40/67* | (2018.01) |
| *G06Q 20/14* | (2012.01) |
| *G06F 19/00* | (2018.01) |
| *A61B 5/00* | (2006.01) |
| *G06Q 50/22* | (2018.01) |
| *G16H 10/60* | (2018.01) |

(Continued)

(52) U.S. Cl.
CPC ............ *G16H 40/67* (2018.01); *A61B 5/411* (2013.01); *G06F 19/00* (2013.01); *G06F 19/3418* (2013.01); *G06Q 20/14* (2013.01); *G06Q 50/22* (2013.01); *G16H 10/60* (2018.01); *A61B 5/0013* (2013.01); *A61B 5/021* (2013.01); *A61B 5/024* (2013.01); *A61B 5/1172* (2013.01); *A61B 5/145* (2013.01); *A61B 5/14532* (2013.01); *A61B 5/7465* (2013.01); *A61B 7/04* (2013.01)

(58) Field of Classification Search
CPC ............ G06F 19/3418; G06F 19/3456; G06F 19/328; G06F 19/321; G06F 19/3462; G06F 19/3481; G06F 19/34; G06F 19/00; G06F 16/951; G06F 16/24578; G06F 16/29; G06F 19/325; G06F 21/32; G06F 21/6245

See application file for complete search history.

(56) References Cited

U.S. PATENT DOCUMENTS

| | | | |
|---|---|---|---|
| 7,613,620 | B2 | 11/2009 | Salwan |
| 7,752,080 | B1 | 7/2010 | Greener |

(Continued)

OTHER PUBLICATIONS

Computer Architecture, Hennessy, Fourth Edition, 2007.

*Primary Examiner* — Maroun P Kanaan
(74) *Attorney, Agent, or Firm* — Law Office of Dorian Cartwright; Dorian Cartwright (57) ABSTRACT

An apparatus and method are provided for treating a healthcare patient. The method includes the steps of establishing an audio/visual teleconference between a processor of the patient at a first location and a processor of a physician located at a second, remote location different from the first location and displaying a set of biometric parameters of the patient in real time to the physician at the remote location.

13 Claims, 2 Drawing Sheets

Related U.S. Application Data

No. 13/421,454, filed on Mar. 15, 2012, now Pat. No. 10,007,761, and a continuation-in-part of application No. 12/408,225, filed on Mar. 20, 2009, now abandoned.

(60) Provisional application No. 61/038,295, filed on Mar. 20, 2008.

(51) Int. Cl.
*A61B 7/04* (2006.01)
*A61B 5/021* (2006.01)
*A61B 5/024* (2006.01)
*A61B 5/1172* (2016.01)
*A61B 5/145* (2006.01)

(56) References Cited

U.S. PATENT DOCUMENTS

| | | | |
|---|---|---|---|
| 7,818,183 B2 | 10/2010 | Schoenberg | |
| 7,835,926 B1 | 11/2010 | Naidoo et al. | |
| 2001/0000045 A1 | 3/2001 | Yu | |
| 2002/0024375 A1 | 2/2002 | Asano | |
| 2002/0198473 A1 | 12/2002 | Kumar | |
| 2003/0028399 A1 | 2/2003 | Davis et al. | |
| 2003/0069752 A1* | 4/2003 | LeDain | G06F 19/3418 705/2 |
| 2004/0210458 A1 | 10/2004 | Evans et al. | |
| 2004/0233894 A1 | 11/2004 | Rutland | |
| 2006/0064326 A1 | 3/2006 | Tucker | |
| 2006/0106290 A1 | 5/2006 | Bulat | |
| 2006/0277075 A1 | 12/2006 | Salwan | |
| 2008/0004904 A1 | 1/2008 | Tran | |
| 2008/0201429 A1 | 8/2008 | Barbell et al. | |
| 2008/0221399 A1 | 9/2008 | Zhou et al. | |
| 2008/0243548 A1 | 10/2008 | Cafer | |
| 2008/0275311 A1 | 11/2008 | Haq | |
| 2009/0054735 A1 | 2/2009 | Higgins | |
| 2013/0278427 A1 | 10/2013 | Setton | |
| 2015/0019231 A1* | 1/2015 | Sadler | G06Q 50/22 705/2 |

* cited by examiner

METHOD AND APPARATUS FOR SHARING MEDICAL INFORMATION

CROSS-REFERENCE TO RELATED APPLICATIONS

This application is a continuation of U.S. patent application Ser. No. 15/996,474, filed, Jun. 2, 2018 which is a continuation of U.S. patent application Ser. No. 13/421,454, filed, Mar. 15, 2012, which is a continuation-in-part of U.S. patent application Ser. No. 12/408,225, filed on Mar. 20, 2009, now abandoned, which claims the benefit of U.S. Provisional Application No. 61/038,295, filed on Mar. 20, 2008, the contents of each being incorporated herein by reference in their entirety.

FIELD OF THE INVENTION

The field of the invention relates to teleconferencing systems are more particularly to methods of using teleconferencing to diagnose medical conditions.

BACKGROUND

Methods of teleconferencing are generally known in the art. Such methods are typically used by businesses to allow a number of people to simultaneously interact through a voice or audio/video connection in order to solve some particular problem.

In order to set up a teleconference connection, each person is typically given a telephone number associated with a conferencing bridge within the telephone network. As each person calls into the conferencing bridge, a processing unit combines the voice information from each caller, normalizes the volume and retransmits the combined and normalized voice signal to each conference participant.

Audio/video conferencing may also be accomplished through the Internet. In this case, an audio/video connection may be formed between two computers. A camera and microphone is connected to each computer. A conferencing application within the respective computers forms a packet connection between the computers. Once the connection is set up, audio and video from each end may be collected from the cameras and microphones, packetized and sent to the other end under a TCP/IP or streaming format.

While prior art methods are effective, they lack flexibility. Because such methods are intended primarily for voice or for voice and video, they are not able to handle information content that cannot easily be supplied through the camera or microphone.

Where the exchange of other information is needed, then other methods must be used (e.g., e-mail, fax, etc.). Because of the importance of communication a need exists for conferencing methods that are adaptable to the needs of the medical community.

SUMMARY

An apparatus and method is provided for treating a healthcare patient. The method includes the steps of establishing an audio/visual teleconference between a processor of the patient at a first location and a processor of a physician located at a second, remote location different from the first location and displaying a set of biometric parameters of the patient in real time to the physician at the remote location.

In another aspect, the apparatus includes a website, a conferencing application at the website that establishes a audio/visual teleconference between a processor of the patient at a first location and a processor of a physician located at a second, remote location different from the first location and a data processing application at the website that displays a set of biometric parameters of the patient in real time to the physician at the remote location.

DETAILED DESCRIPTION OF AN ILLUSTRATED EMBODIMENT

Figure 1:
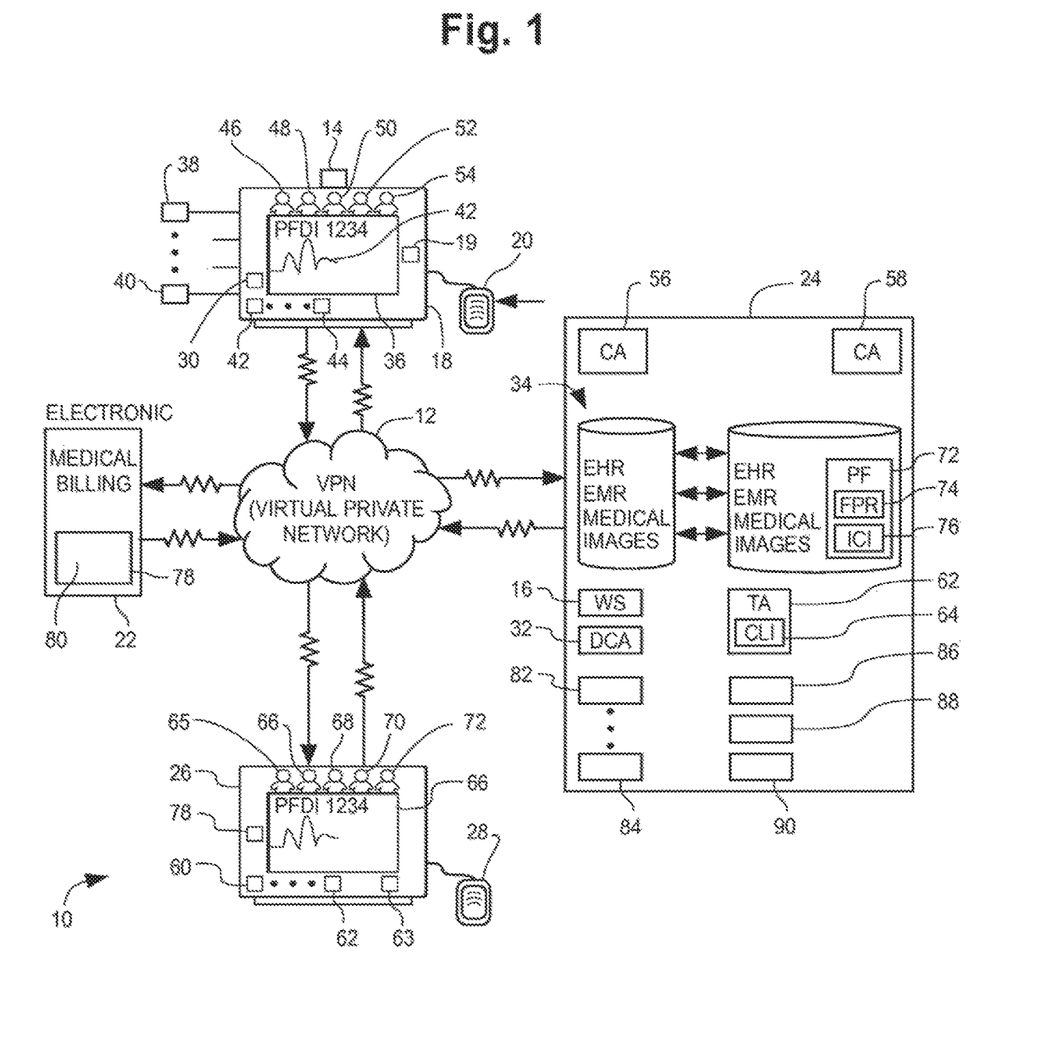
FIG. 1 is a block diagram of a telemedicine system in accordance with an illustrated embodiment of the invention and FIG. 2 is a flow chart of process steps that may be used by the system of FIG. 1.
Figure 2:
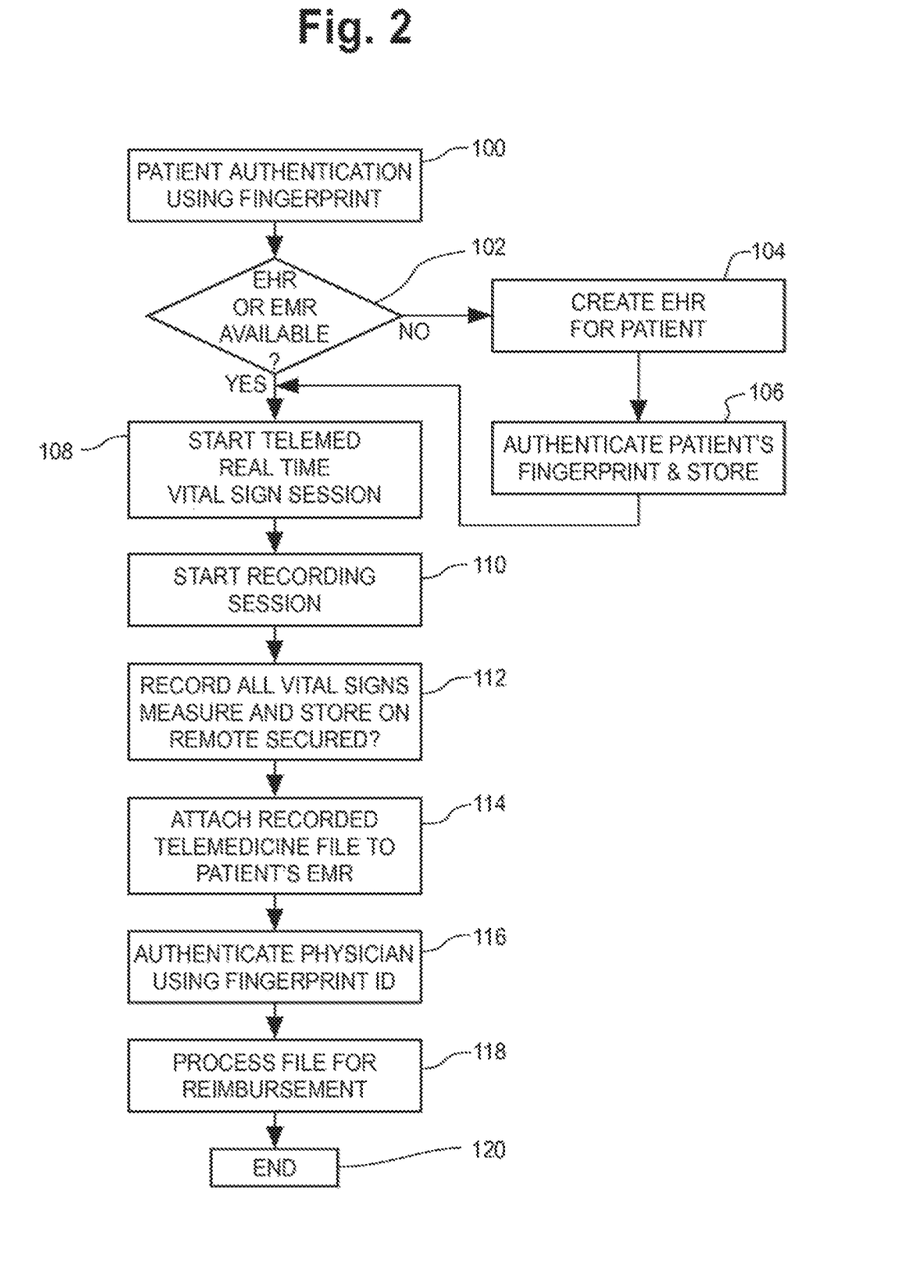

FIG. 1 is a block diagram of a medical conferencing system 10 shown generally in accordance with an illustrated embodiment of the invention. FIG. 2 is a flow chart of method steps that may be used within the system 10.

The system 10 may include a caregiver's computer 18, the computer 26 of a consultant 26, a host 24 and other computer devices described in more detail below. Included within the computers 18, 26, 24 (and the other devices) may be one or more processors (implemented as hardware) operating under the control of one or more computer programs (applications) loaded from a non-transitory computer readable medium (memory). In the description below, any reference to an application is also a reference to the hardware of the processor upon which the application executes and provides which provides the functionality described.

The system 10 may be used by a patient alone or by patient with the help of a caregiver to share health information with any of a number of healthcare consultants (e.g., physicians). The sharing of information by the system 10 is based upon the use of a website 16 within a host 24 that the patient or the patient and caregiver (the patient or patient and caregiver together hereinafter referred to as the "caregiver") sign into. Signing into the system 10 may include verification 100 of a patient's identify through the use of a fingerprint scanner 20.

Once a patient has signed into the system 10 using the fingerprint scanner 20, the fingerprint of the patient may be compared with a file copy 74 to verify the identity of the patient. The registration or recognition of the patient is a prerequisite that allows the system 10 to begin 108 a conference between the caregiver 18 and one or more consultants.

The caregiver's computer 18 may be provided in any of a number of different forms (e.g., notebook computer, personal digital assistant (PDA), etc.) The caregiver's computer 18 may be used in conjunction with virtual private network (VPN) software including a FOB 14 attached to the computer 18 that allows the computer to securely sign into the website 16 within a VPN 12.

The website or web portal allows the caregiver 18 to send text messages, medical images or other medical data via a chat functionality. The caregiver 18 and VPN 12 allow private chat conversations including video, audio and text.

Once the caregiver 18 signs into the system 10, a data handling application 32 associated with the website 16 of the host 24 determines whether 102 the patient has previously registered with the system 10 and whether an electronic health record 72 exits for this patient. If not, then the application 32 creates 104 a record. As part of that creation, the patient is asked to insert his/her finger in the fingerprint scanner 20 to authenticate 106 the identity of the patient.

Once signed in, one or more conferencing applications 42, 44 within the caregiver's computer 18 may begin exchanging information with other parties to the conference through the website 16. In addition, a data collection application 30 within the caregiver's computer 18 may begin sending copies of biometric information appearing on the caregiver's computer screen 36 and/or changes to the biometric information to the website. A corresponding data handling application (e.g., 32) associated with the website 16 may begin saving the screens from the caregiver's computer into an archive database 34. The database 34 may maintain a file 72 of saved information for each patient.

The saving of the caregiver's screens allows the caregiver to locally connect the caregiver's computer to any of a number of different diagnostic equipment 38, 40 that may be used to display biometric parameters 42 of the patient within a display window 36. Since the communication application 30 copies the information within the window 36, the software supplied with the diagnostic equipment may be used without modification to share and archive the patient's biometric information.

The diagnostic equipment 38, 40 may be selected from any of a number of different medical imaging and/or testing devices. Examples include heart rate monitors, portable ultrasound probes, portable X-ray machines, glucose monitors, chemical dependency test systems, infection disease test systems, blood analysis systems, spirometers, digital weight scales, digital thermometers, blood pressure monitors, exercise monitors, digital peak flow meters, pulse oximeters, digital stethoscopes, high resolution medical cameras, high resolution ophthalmology cameras, high resolution ear, nose and throat camera and apparatus, digital range of motion devices used on flexible joints or digital infection detection test devices.

In addition to archiving 110 the patient's biometric information, the conferencing applications 42, 44 allow the caregiver to set up video conferences with one or more healthcare professionals (physicians) for purposes of consulting. Consulting in this case means viewing the biometrics of the patient in real time while also conversing in real time with the healthcare provider and/or patient. In order to preserve patient privacy, a consultant 26 may also be required to identify himself/herself 116 to the consultant's computer 26 via a fingerprint scanner 28.

The fingerprint scanners or readers 20, 28 authenticate the patient, home healthcare worker and healthcare professional at a login prompt presented by the website 18. The software of the computer 18, 26 allows participants to share and view their respective computer desktops with all or selected participants. The software also allows the content of the conference to be recorded and stored on a central data repository system 34. The website 16 and associated processes of the central data repository are used to collect, process and store the electronic heath records for each patient within a respective file 72. Stored data may include, but is not limited to, medical images, physician's notes, video, audio and text and may be stored within (or in conjunction with) each patient's record. Once a patient's fingerprint has been identified to the system 10, the patient's existing electronic health records (EHR) and electronic medical records (EMR) can be retrieved and correlated to a current session of stored information.

The system 10 also automatically generates and processes an electronic bill to the patient's healthcare provider 22 for prompt payment. This can be accomplished using the physician's fingerprint and digital signature for authentication purposes. The system 10 can access and update a patient's medical records with strict access rights and privileges. The secure data base 34 may process and store medical records including, but not limited to magnetic resonance imaging data, computed tomography image data, X-ray imaging data, positron emission image data, ultrasound image or sonography data, heart rate data, blood glucose data, body weight data, body mass index data, date of birth, patient identification number, personal contact information, allergy information, medication history, family/personal physician's name, family/personal car physician's identification number, recorded telemedicine virtual visit sessions (conferences), asthma data, pulse oximeter data, blood analysis data, body temperature, blood analysis data, physician notes, referring physician notes, medical specialist notes and medical history data.

The caregiver's computer 18 may also provide preconfigured documentation templates 82, 84, including procedural notes, real-time vital sign diagnostic flow sheets and graphs, summaries and care plans for commonly encountered problems in chronic disease management which may also, in turn, require critical care, emergency care, ambulatory care and acute care physician visits. Temples 82, 84 may be accessed through the website 16 for use during conferences between participants.

Each caregiver (by specialty) can easily configure these templates 82, 84 generated by the computer 18 to meet specific needs and can create standardized and scalable electronic health and electronic medical records. Based upon care plans and protocols, embedded physician and nursing documentation on medical conditions and treatment options can function to prompt caregivers as they navigate through pathways of care and alert them to tasks needing action prospectively. Physician documentation or resources available through the website 16 may ask for or prompt the physician with E&M coding that shows the documentation level of each visit. The system 10 may also recommends an appropriate CPT code to ensure timely and accurate billing.

The actual consultations with physicians or other healthcare workers may be recorded to allow future caregivers to review the video and audio in conjunction with the documentation templates. The recordings serve as a back-up to reduce the number of patient errors, fraud and to improve overall efficiency.

Communication between the caregiver's computer 18 and website 18 may occur using a broadband access device, DSL, dial-up or cable internet through the world wide web. Once a secure internet connection is set up, the caregiver and the patient are able to access the website 18 to conduct a teleconference medical (telemedicine) consultation through the VPN 12.

The system 10 may use voice recognition software 86 to transcribe the health provider's spoken words into written text. The recorded voice and text may both be saved into the patient's medical records 72.

The database 34 may also contain identifying information of every known medication listed in the Physician's Desk Reference 88. Both PDR illustrations and explanations of each medication are accessible through the website 16 to the physician, patient, pharmacist and other health care professional that use the system 10. Using proprietary image processing software 90, each medication is recognized by the camera 14 and a list of medications along with each PDR picture of the medication is retrieved to verify the accuracy of the medication presented by the patient and/or home health care provider assisting the patient. An image or identifier of each recognized medication may be saved to the file 72.

The caregiver computer 18 may be installed in emergency vehicles, cars, trucks, recreational vehicles, airplanes, military vehicles and helicopters. The system 10 can also be installed in public areas for emergency access by a physician or other emergency health care professional.

The system 10 can be used by homebound patients, hospitals, dialysis centers, or skilled nursing centers from anywhere in the world. This availability is fostered by access through the internet and allows telemedicine sessions to be conducted from anyplace in the world.

Data transmission and storage in the system 10 is 256 bit data encrypted to protect the patient's privacy. Additionally, data stored on the secure data base repository system 34 is backed up as shown in FIG. 1 through the use of a redundant data base system stored at a separate secure location. Patient data can only be retrieved by authorized medical professionals, patients and family members.

In order to conference in a consultant, the healthcare provider may use a process similar to WebX for conferencing. In this case, however, the conference may be set up using a real time message (e.g., a chat message) through the website.

In order to invite a consultant to join the conference, the healthcare provider may select consultants from a menu of consultants and activate an invite softkey for each consultant to be added to the conference. Upon activation of the invite softkey, the conferencing application 42, 44 opens a respective consultant viewing window 46, 48, 50, 52, 54 and sends a chat message to the website 16 identifying the consultants and a respective audio/video port within the caregiver's computer for use during that consultation. The website 16, in turn, may activate a respective conference handling application 56, 58 for each consultant and forward the message to a respective computer 26 of the selected consultants.

A tracking application 62 associated with the website 16 may also maintain a tracking list 64 of consultants. In addition to maintaining a tracking list of consultants, the tracking application 62 may also assign a unique identifier to the conference and associate that unique identifier with the identifier of the patient.

If the consultant accepts the conferencing offer, a corresponding communication application 60 within a computer 26 of the consultant may send an acceptance message to the website 16. The invite message from the website 16 to the consultant may identify a communication audio/video port of the conferencing application 56, 58 for use during the conference. The acceptance message from the consultant returned to the website 16 may identify a corresponding communication port within the conferencing application 60 of the consultant. Upon receipt of the acceptance message from the consultant by the website, the website may send an acceptance message to the caregiver's computer identifying an audio/video port on the activated conferencing application 56, 58 associated with the consultant. The identified port of the consultant is also added to the tracking list 64.

In addition to responding to the invite, the consultant's computer may also activate a video camera and microphone. Once activated, the consultant's computer may begin sending audio and video packets to the identified port of the respective conference handling application 56, 58. The conferencing application 56, 58 may receive the audio and video packets from the consultant and forward them to the identified port of the conferencing application 42, 44 within the caregiver's computer 18. In addition to forwarding the audio and video packet to the caregivers computer 18, the respective conferencing application 56, 58 also forwards the audio and video packets to the respective receive ports of any other consultant present within the tracking list 64.

Similarly, once the consultant viewing application 42, 44 within the caregiver's computer begins receiving audio/video from the consultant 26, the conferencing application 42, 44 may open a viewing window 46, 48, 50, 52, 54 and begin displaying video from the consultant in the opened window. The caregiver computer may also activate a video camera and microphone and begin collecting audio/video information regarding the caregiver and/or patient. The collected audio/video is transferred through the identified port of the caregiver's computer to the corresponding identified port of the conferencing application 56, 58 of the website. The website in turn forwards the audio/video to the consultant's computer and two-way audio/video communication is established.

Once the two-way audio/video connection is established, the caregiver/patient may begin conversing with the consultant 26. As noted above, the conferencing application (e.g., 42) opens a first consultant window (e.g., 46) on the display of the caregiver's computer. Within the first consultant window 46, the consultant viewing application displays video from the consultant's computer while at the same time routing audio from the consultant to a sound card within the caregiver's computer 18. At the same time the video camera and microphone collects audio/video of the caregiver/patient and forwards the audio/video to the consultant.

In addition to displaying audio and video from the caregiver/patient 18, each consultant 26 also displays audio and video from any other consultant 26 that has accepted an invitation from the caregiver/patient 18. In this case, the audio and video from each consultant 26 is forwarded to any other consultant present within the tracking list 64. Upon receipt of audio and video from other consultants 26, a new conferencing application 62 and window 65, 66, 68, 70, 72 is opened so that each consultant would hear and observe any other consultant that is added by the caregiver/patient 18 to the conference.

During the conversation, the consultant or caregiver may determine that further biometric information may need to be collected from the patient. In this case, the caregiver may connect one or more biometric parameter collection devices 38, 40 to the caregiver's computer 18. In this case, the connection to the biometric parameter collection device 38, 40 may be established through an appropriate connection (e.g., serial, parallel, USB, firewire, etc.) on the caregiver's computer 18. Software associated with the biometric parameter collection device 38, 40 may open a window 36 on the caregiver's computer 18 that displays the biometric parameters to the caregiver.

The opening of the window 36 for display of the biometric parameters of the patient is independent of the consultant windows 46, 48, 50, 52, 54 displaying audio/video from the consultants. The caregiver may adjust the size of the biometric window 36 as appropriate for viewing convenience.

Once the biometric window 36 has been opened, the caregiver may also activate the data collection application 30. Once activated, the data collection application 30 captures 112 any information presented within the window 36 and forwards the captured information to the data collection application 32 where the captured information is associated 114 with the patient file 72. The captured information is archived as discussed above and is also sent to any consultant present within the tracking list 64. In this regard, the receipt of captured data from the data handling application causes the activation of a corresponding data display application 63 and the opening of a data display window 65 on the consultant's computer.

The captured information from the biometric window 36 may be archived in the database 34 in the patient file 72 or under the unique identifier assigned by the tracking application 62 for use in conjunction with the patient data file 72. The tracking application may also save the audio and video of the caregiver/patient 18 and of each consultant 26 under that same identifier as well as save the start and ending times of the conference and identifiers of the individual consultants.

Also associated with each consultant terminal 26 (or website 16) is a billing application 78. Periodically, the consultant may activate the billing application 78 and enter an identifier of a patient or the unique identifier of the conference assigned by the tracking application 62. In response, the billing application 78 may retrieve an identifier 76 of an insurance carrier (or other responsible party) and the time spent by the consultant during conferences with the identified patient. The billing application 78 may also retrieve the audio and video from the conference for viewing by the consultant in the case where the consultant no longer remembers the subject matter of the conference.

The billing application 78 may also process 120 the file 72 and generate an invoice or bill 78 pre-populated with the relevant information including the patient name, the physician's name and identifier and conference times. The consultant 26 may enter the appropriate billing codes (e.g., evaluation and maintenance (E&M) codes, current procedural terminology (CPT) codes, etc.) 80. Once an invoice is completed, the billing application 78 may automatically submit the invoices to the insurer 22 or other responsible party for payment.

The system 10 offers significant advantages over prior art systems. In the case of bedridden patients, the system 10 allows one or more consultants to converse and view biometric parameters of the patient without having to be in the same room as the patient. Similarly, consultants can join a conference from whatever location is convenient for the consultant.

Similarly, the biometric window 66 allows any of a number of different biometric parameters to be viewed in real time. Alternatively, past recordings of biometric parameters can be retrieved from a patient record 72 for comparison with current readings.

In one aspect, the conferencing system 10 uses the system of FIGS. 1 and 2 for providing a method of treating a healthcare patient. The method may be practiced as follows. For example the system may operate by first establishing an internet connection using a high-performance single issue Central Processing Unit (CPU) within the caregiver's computer 18 and which is integrated with a specially designed load-store DLX ("Deluxe") architecture with a pipelining schema which allows multiple instructions to overlap. Every DLX instruction can be implemented in at most five clock cycles. The five clock cycles are as follows: 1. Instruction fetch cycle (IF). 2. Instruction decode/register fetch cycle (ID). 3. Execution/effective address cycle (EX). 4. Memory Access/branch completion cycle (MEM). 5. Write-back cycle (WB). The operating speed of the CPU is equal to or greater than 1.2 GHz. The computer architecture is comprised of a minimum 16 KB Instruction and a minimum 16 KB Data 4-way, set-associative L1 cache, 256 KB unified 4-way, set-associative L2 cache, 16-bit DDR2 memory interface (up to 800 MHz data rate), two Gigabit Ethernet MACs with interface options, precise timing protocol and audio video bridging, single PCI-Express port, four USB 2.0 ports with integrated PHY, 4 SATA (Serial Advanced Technology Attachment) 2.0 ports with integrated PHYS, network security engine with encryption algorithms, audio and MPEG transport stream interface, two TDM (Time division multiplexing) channels, SDIO (Secure Digital Input Output), NAND flash, SPI (Serial Peripheral Interface), TWSI (Two wire serial interface) and two UART (Universal Asynchronous Receiver/Transceiver) interfaces. The computer architecture is housed in the form factor of a plug computer. The plug computer is programmed to leverage the specially designed loadstore DLX computer architecture. The plug computer is integrated with cellular/mobile communications circuitry. Once the plug computer has established internet connectivity through the network 12 using said cellular/mobile communications circuitry, the plug computer issues several ping commands to a well-known web site such as Google.

Thereafter, using wireless circuitry embedded and Bluetooth (802.1 In wireless) specific algorithms, the plug computer searches for and connects to Bluetooth (802.1 In wireless) enabled medical peripherals which appear in a preconfigured data table. The data table contains the MAC addresses of each medical peripheral along with the name of the medical peripheral and its serial number. The algorithms stored on the plug computer reads the medical peripheral data table and sends data to and receives data from the connected medical peripherals during the communications handshaking process. Once the communications handshaking process has been established between the plug computer and the medical peripherals, the plug computer reads data from the medical peripherals and establishes a Virtual Private Network (VPN) connection before securely transmitting the data to a remote server. The remote server hosts a secure web portal used to store patient vital signs, patient demographics, physician license information, Electronic Medical Records and other patient specific electronic records. The secure web portal is programmed to automatically generate alerts to the patient's primary care physician if the patient's vital readings are outside of the prescribed limits established by the patient's primary care physician. When a patient's vital signs signal an alert, the web server searches a database containing information for the appropriate medical specialists and pharmacists within the patient's health insurance network who can collaborate with the patient and the patient's primary care physician via a secure medical collaboration visit which is comprised of a live Flash enabled streaming audio/visual teleconference between a plug computer of the patient at a first location and a computer capable of receiving and sending live Flash audio/video of a physician located at a second, remote location different from the first location and a computer capable of receiving and sending live Flash audio/video of a physician located at a third location and a computer capable of receiving and sending live Flash audio/video of a physician located at a fourth location and a computer capable of receiving and sending live Flash audio/video of a physician located at a fifth location; displaying a set of biometric parameters of the patient in real time to the physicians at the four remote locations.

A specific embodiment of method and apparatus for conferencing consultants has been described for the purpose of illustrating the manner in which the invention is made and used. It should be understood that the implementation of other variations and modifications of the invention and its various aspects will be apparent to one skilled in the art, and that the invention is not limited by the specific embodiments described.

Therefore, it is contemplated to cover the present invention and any and all modifications, variations, or equivalents that fall within the true spirit and scope of the basic underlying principles disclosed and claimed herein.

I claim:

1. A computer-implemented method, in a computer wirelessly coupled to medical peripherals that are remote from the computer over a data communication network, for monitoring and treating a healthcare patient by healthcare consultants over the data communication network, the method comprising the steps of:
   receiving a selection of healthcare consultants, over the data communication network, from a plurality of available healthcare consultants;
   receiving biometric identification data of the healthcare patient from a biometric sensor;
   authenticating the patient;
   searching for, and wirelessly connecting to, enabled medical peripherals of the patient;
   wirelessly collecting biometric parameters of the healthcare patient from the enabled medical peripherals across the data communication network and remote from the computer;
   responsive to initiating a conference network connection between the computer and the computer for health consultant for an audio/video teleconference between the at least one computer of the healthcare patient at a first location and one or more healthcare consultant located at a second remote location, the second remote location distinct from the first location, displaying images of the healthcare patient along with biometric parameters of the patient in real time with the conference network connection to the computer for the healthcare consultant.

2. The method of claim 1 for treating the patient further comprising:
   setting up a virtual private network between the computer of the patient and the computer for healthcare consultant.

3. The method of claim 1 for treating the patient as in claim 1, wherein the biometric parameters further comprise one selected from of the group consisting of: heart rate, an ultrasound image, an X-ray image, a glucose level, a chemical dependency measurement, an infectious disease measurement, a blood analysis, a spirometric measurement, a weight, a temperature, a blood pressure measurement, an exercise monitoring measurement, a peak flow measurement, on an oximetric measurement, a stethoscope parameter, a high-resolution medical camera image, a high-resolution ophthalmologic image, a high-resolution ear, nose and throat image, a range of motion measurement and an infection detection measurement.

4. The method of claim 1, further comprising:
   wirelessly coupling the enabled medical peripherals for providing the biometric parameters to the computer of the healthcare patient.

5. The method of claim 1 for treating the patient, wherein displaying the biometric parameters of the patient comprises using images from dedicated software associated with the enabled medical peripherals.

6. The method of claim 1 for treating the healthcare patient,
   wherein displaying the biometric parameters comprises images provided by the enabled medical peripherals.

7. The method of claim 1 for treating the healthcare patient,
   wherein displaying the biometric parameters comprises capturing images provided by the enabled medical peripherals as a sequence of real time images.

8. The method of claim 1 for treating the patient, further comprising:
   sending the real time images for display on a website.

9. The method of claim 1 for treating the healthcare patient, further comprising:
   archiving the real time images.

10. The method of claim 1 for treating the patient as in claim 1, further comprising:
    generating and presenting a billing record for the teleconference to the computer of the health care consultant after termination of the teleconference for entry by of evaluation and management (E & M) codes or current procedural terminology (CPT) codes.

11. The method of claim 10, for treating the patient, further comprising:
    automatically generating a services invoice for the teleconference using the E & M or CPT codes from the physician to a health insurer of the patient.

12. A computer for monitoring and treating a healthcare patient over a data communication network, comprising:
    a network interface of the computer receiving a selection of healthcare consultants, over the computer network, from a plurality of available healthcare consultants;
    a fingerprint scanner to receive biometric identification data from the healthcare patient for authenticating the healthcare patient;
    a connection port of the computer to search for and connect to enabled medical peripherals to collect biometric parameters from the enabled medical peripherals;
    a processor of the computer to, responsive to initiating a conference network connection between computer and the computer for the health consultant, display images of the healthcare patient along with the biometric parameters of the healthcare patient in real time to the computer for healthcare consultant.

13. A non-transitory computer-readable medium storing source code that when executed by a processor performs a method, in a computer wirelessly coupled to medical peripherals that are remote from the computer over a data communication network, for monitoring and treating a healthcare patient by healthcare consultants over the data communication network, the method comprising the steps of:
    receiving a selection of healthcare consultants, over the data communication network, from a plurality of available healthcare consultants;
    receiving biometric identification data of the healthcare patient from a biometric sensor;
    authenticating the patient;
    searching for, and wirelessly connecting to, enabled medical peripherals of the patient;
    wirelessly collecting biometric parameters of the healthcare patient from the enabled medical peripherals across the data communication network and remote from the computer;
    responsive to initiating a conference network connection between the computer and the computer for health consultant for an audio/video teleconference between the at least one computer of the healthcare patient at a first location and one or more healthcare consultant located at a second remote location, the second remote location distinct from the first location, displaying images of the healthcare patient along with biometric parameters of the patient in real time with the conference network connection to the computer for the healthcare consultant.

\* \* \* \* \*

UNITED STATES PATENT AND TRADEMARK OFFICE
CERTIFICATE OF CORRECTION

| | | |
|---|---|---|
| PATENT NO. | : 10,790,059 B2 | Page 1 of 1 |
| APPLICATION NO. | : 16/785375 | |
| DATED | : September 29, 2020 | |
| INVENTOR(S) | : Sherrod A. Woods | |

It is certified that error appears in the above-identified patent and that said Letters Patent is hereby corrected as shown below:

On the Title Page

Item (12): should read Woods et al.

Item (72): after "(US)" insert -- Errick Sadler, Florissant, MO (US); Melanie Mencer-Parks Pearland, TX (US); William Langford, Morrisville, NC (US); Randy S. Sessler, Mentor, OH (US); Joseph Boucree, Baton Rouge, LA (US) --

Signed and Sealed this
Twenty-seventh Day of September, 2022

*Katherine Kelly Vidal*

Katherine Kelly Vidal
*Director of the United States Patent and Trademark Office*